US010585270B2

(12) United States Patent
Tykocki et al.

(10) Patent No.: US 10,585,270 B2
(45) Date of Patent: Mar. 10, 2020

(54) REFLECTED IMAGE MACROSCOPY SYSTEM

(71) Applicant: The University of Vermont and State Agricultural College, Burlington, VT (US)

(72) Inventors: Nathan R Tykocki, Essex Junction, VT (US); Grant Hennig, Essex Junction, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 16/170,207

(22) Filed: Oct. 25, 2018

(65) Prior Publication Data

US 2019/0121109 A1 Apr. 25, 2019

Related U.S. Application Data

(60) Provisional application No. 62/576,845, filed on Oct. 25, 2017.

(51) Int. Cl.
| | |
|---|---|
| *G02B 21/00* | (2006.01) |
| *G01N 21/64* | (2006.01) |
| *G02B 21/06* | (2006.01) |
| *G02B 21/18* | (2006.01) |
| *G02B 27/10* | (2006.01) |
| *G02B 27/14* | (2006.01) |

(52) U.S. Cl.
CPC ..... *G02B 21/0028* (2013.01); *G01N 21/6458* (2013.01); *G02B 21/008* (2013.01); *G02B 21/06* (2013.01); *G02B 21/18* (2013.01); *G02B 27/1066* (2013.01); *G02B 27/143* (2013.01); *G01N 2021/6482* (2013.01)

(58) Field of Classification Search
CPC ....... G01N 2021/6482; G01N 21/6458; G02B 21/0028; G02B 21/008; G02B 21/06; G02B 21/18; G02B 27/1066; G02B 27/143

See application file for complete search history.

(56) References Cited

U.S. PATENT DOCUMENTS

| 6,803,205 B2 * | 10/2004 | Duffy | G06T 7/70 |
| | | | 435/15 |
| 9,743,020 B2 * | 8/2017 | Zheng | G02B 21/36 |
| 2012/0133740 A1 * | 5/2012 | Klimov | G01N 21/6458 |
| | | | 348/46 |

(Continued)

*Primary Examiner* — Marcus H Taningco

(57) ABSTRACT

A multi-plane imaging system for imaging multiple reflection planes of a regular or irregular shaped three-dimensional (3D) specimen having top, side and bottom views simultaneously. The system includes an inverted watertight pyramid well having at least four reflective side surfaces for reflecting the specimen side views, wherein each of the at least four reflective sides surfaces define an angle, θ, relative to the base horizontal plane, and wherein each reflective side surface comprises a plurality of reflective zones; A specimen is positioned horizontally equidistant from the at least four reflective side surfaces and positioned vertically from the base horizontal plane a predetermined vertical distance; wherein the predetermined vertical distance, the at least four reflective side surfaces, and the angle θ comprise a reflection image plane for reflecting the specimen bottom views.

13 Claims, 1 Drawing Sheet

(56) References Cited

U.S. PATENT DOCUMENTS

| | | | |
|---|---|---|---|
| 2013/0143165 A1* | 6/2013 | Seale | G02B 21/04 |
| | | | 430/323 |
| 2014/0133623 A1* | 5/2014 | Creux | G01N 23/046 |
| | | | 378/19 |
| 2016/0109357 A1* | 4/2016 | Lorbeer | G02B 21/34 |
| | | | 250/576 |
| 2016/0206208 A1* | 7/2016 | Yamamoto | A61B 5/0066 |
| 2016/0214107 A1* | 7/2016 | Viasnoff | G01N 21/03 |
| 2018/0045622 A1* | 2/2018 | Deisseroth | B01L 3/502 |

* cited by examiner

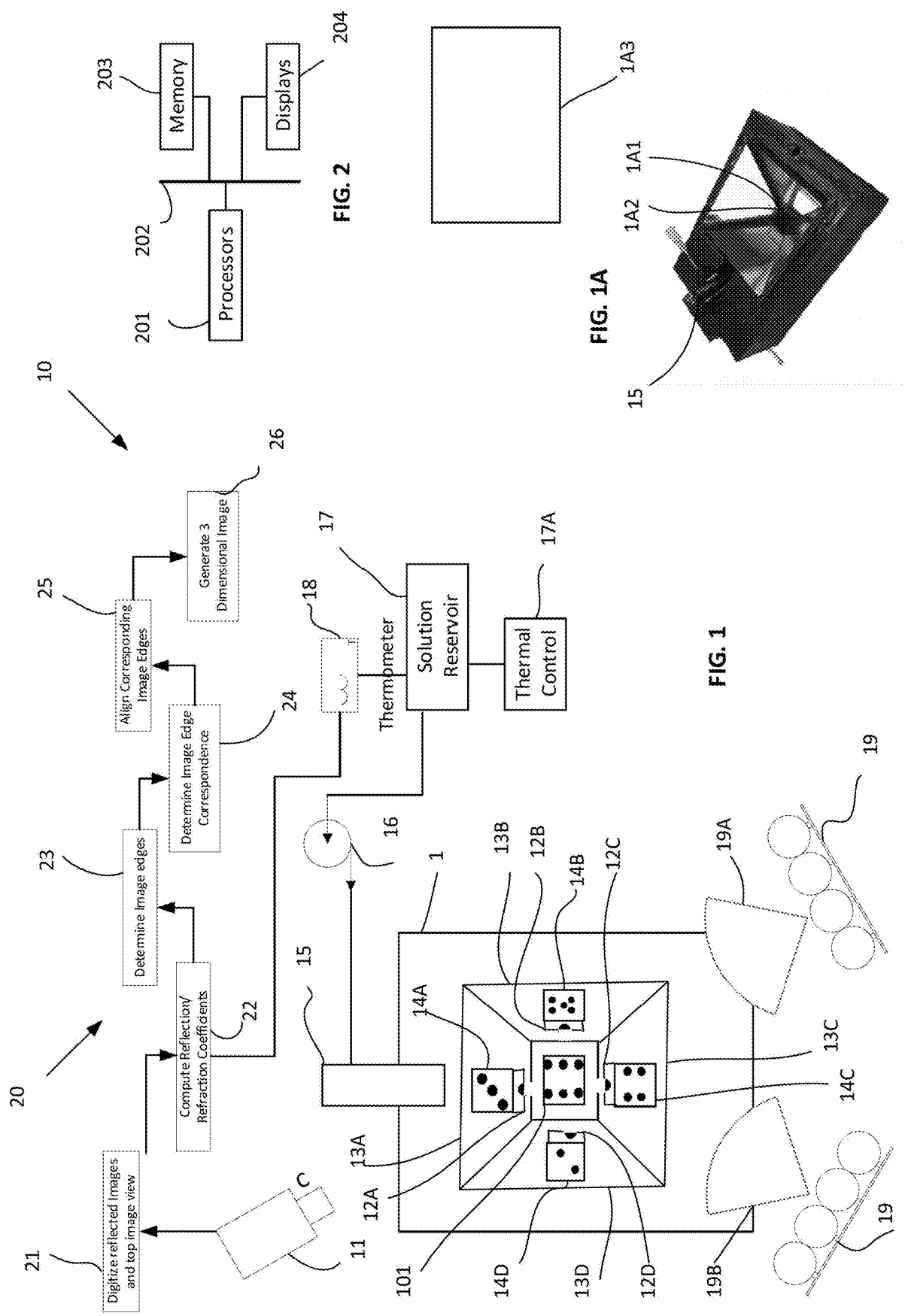

REFLECTED IMAGE MACROSCOPY SYSTEM

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. provisional patent application 62/576,845, entitled "REFLECTED IMAGE MACROSCOPY SYSTEM", naming Nathan Tykocki and Grant Hennig and as inventors, filed 25 Oct. 2017.

STATEMENT REGARDING GOVERNMENT LICENSE RIGHTS

"This invention was made with government support under DK-103840 awarded by NIH-NIDDK. The U.S. government has certain rights in the invention."

BACKGROUND

1. Field of Use

The invention relates to 3D imaging in general and more particularly to a device for imaging 6 planes of an object simultaneously.

2. Description of Prior Art (Background)

Of growing interest in modern microscopy is three-dimensional (3D) microscopy, which acquires three-dimensional image with every image plane sharply in focus. This is in contrast to conventional microscopy where the image of in-focus plane is superposed with blurred image of out-of-focus planes. Several developments of 3D microscopy have been reported. These techniques have been gaining popularity in the scientific and industrial communities. Typical applications include life sciences and semiconductor inspection.

In one development an inverted microscope is a microscope with its light source and condenser on the top above the stage pointing down, and the objectives and turret are below the stage pointing up. Inverted microscopes are useful for observing living cells or organisms at the bottom of a large container (e.g. a tissue culture flask) under more natural conditions than on a glass slide, as is the case with a conventional microscope.

In confocal scanning microscopy (CSM), the out-of-focus signal is spatially filtered out by confocal aperturing of the object illumination and the detector points. The 3D image is constructed by pixel-by-pixel mechanical scanning of the entire object volume, which places a fundamental limit on the image acquisition speed.

Therefore, a heretofore unaddressed need exists in the art to address the aforementioned deficiencies.

BRIEF SUMMARY

A system for imaging 6 planes of an object simultaneously over time for 3-D and 4-D reconstruction of the object's position, size, motion and location. Allows for rapid and reproducible measurement of small changes in an object's shape over time; e.g., micro-motions of a bladder wall during bladder filling. Instead of a single focal plane, end users could now see 6 planes simultaneously and reconstruct a 3-D mesh of the object and see changes over time.

The invention is directed towards a multi-plane imaging system for simultaneously imaging multiple reflection planes of a regular or irregular shaped three-dimensional (3D) specimen. The 3D specimen includes top, side and bottom views viewed simultaneously. The system includes a body comprising a base having a base horizontal plane. The body also includes an inverted watertight pyramid well having at least four reflective side surfaces for reflecting the specimen side views. Each of the at least four reflective sides surfaces define an angle, $\theta$, relative to the base horizontal plane, and each reflective side surface comprises a plurality of reflective zones. The body also includes a specimen mounting system positioned horizontally equidistant from the at least four reflective side surfaces; and, positioned vertically from the base horizontal plane a predetermined vertical distance. The aforementioned predetermined vertical distance, the at least four reflective side surfaces, and the angle $\theta$ comprise a reflection image plane for reflecting the specimen bottom views. The system also includes a solution controller for regulating a solution in the inverted watertight pyramid well. The multi-plane imaging system also includes a non-transitory computer readable storage medium having computer readable code thereon, the medium including instructions in which a computer processor performs operations for rendering and displaying a 3D image of the specimen. The instructions also include determining an index of refraction associated with the regulated and illuminated first solution.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 schematically depicts a mirrored pyramidal well and image collection system according to one embodiment of the present invention;

FIG. 1A is a pictorial representation of the schematically depicted well illustrated in FIG. 1; and FIG. 2 is a block diagram of a system configuration of an image processing system according to the invention shown in FIG. 1.

DETAILED DESCRIPTION

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Referring now to FIG. 1 of the drawings, there is shown a schematically depicted mirrored pyramidal well and image collection system 10 according to one embodiment of the present invention. The system 10 includes well body 1, reflection surfaces 13A-13D, illumination system 19, solution input body port 15, solution pump 16, solution reservoir 17, thermal control 17A, and solution thermometer 18. It will be appreciated that reflection surfaces 13A-13D are positioned to form an inverted pyramidal shape.

Also shown in FIG. 1 is sample object 101 and its side image reflections 14A-14D imaged upon corresponding reflection surfaces 13A-13D. FIG. 1 also shows images 12A-12D, each representing a partial view portion of the object 101 bottom view. It will be appreciated that the object 101 bottom view may be reconstructed with opposing view portions (e.g., 12A and 12C, or 12B and 12D), or all partial view portions (12A-12D). It will be further understood that object 101, while shown as a die in the drawings to illustrate the reflection characteristics of reflection surfaces 13A-13D, may be any object or specimen, including living specimens (e.g., bladders, cells, cancer cells, etc). It will be further understood that a bottom reflective surface (not shown) may be located underneath the specimen holder.

System 10 also includes an imaging device 11 and a body of instructions 20 for rendering the simultaneous views (e.g., 14A-14D and 12A-12D) and a top view as seen by imaging device 11. The body of instructions digitizes 21 all views and computes 22 the refraction/reflection coefficients based upon a given refractive index associated with the solution in solution reservoir 17. System 10 further determines 23 the edges of all images, determines corresponding image edges 24, aligns the corresponding edges 25, and generates a 3D image for display on display device(s) (FIG. 2-204).

Referring still to FIG. 1 and also FIG. 1A there is shown solution input body port 15, pyramidal input port 1A1, and specimen or object mount 1A2. In operation solution is pumped from solution reservoir 17 via pump 16 to body input port 15 and to pyramidal input port 1A1, underneath the specimen or object (e.g., 101). It will be appreciated that flow solution into pyramidal input port 1A1 at the bottom of the inverted pyramidal well allows for a controlled, gentle rise of the solution from the bottom of inverted pyramidal well.

Still referring to FIG. 1, solution reservoir 17 may contain any suitable solution or medium such as for example saline, glucose solution, or gas. Solution reservoir is thermally controlled by thermal control device 17A and information identifying solution time and thermal state are communicated to body of instructions 20 for calculating reflections/refractions, and rendering a 3D view. It will also be appreciated that the thermal control device and solution reservoir operate to provide a desired in vivo environment for object or specimen 101.

Still referring to FIG. 1A it will be appreciated that object mount 1A2 may be any suitable object mount minimizing imaging distortion or preventing reflective surfaces 13A-13D from "seeing" an objects bottom view. For example, object mount 1A2 may be a thin mounting wire or clear sample slides (e.g., clear glass or plastic). In addition, object mount 1A3 may also rotate at fixed or varied revolutions per minute (RPMs).

Still referring to FIG. 1A. there is shown well cover 1A3. Well cover 1A3 is adapted to fit over the inverted well formed by reflective surfaces 13A-13B to prevent evaporation of the solution or gas from the inverted well. In addition, well cover 1A3 may be any suitable cover such as, for example, clear glass or a light filter (e.g., UV filters or polarizing filter). Well cover 1A3 may also be a magnifying glass cover, thus reducing or minimizing the need for an expensive imaging device have high resolution.

Still referring to FIG. 1, imaging device 11 may be any suitable imaging device or combination of devices, such as, for example, a light imaging device (e.g., a digital single lens reflex camera, USB camera, or video camera), a thermal imaging device, and/or a charged coupled device (CCD).

Still referring to FIG. 1, illumination system 19 may include any suitable illumination spectrum, such as, for example, white light or fluorescent emitters.

Referring also to FIG. 2 there is shown a block diagram of a system configuration of an image processing system according to the invention shown in FIG. 1. Processor 201, display 204, and main memory 203 are connected to local bus 202. Main memory 203 may include an integrated memory controller and cache memory for processor 201. Additional connections to local bus 202 may be made through direct component interconnection or through add-in boards.

Main memory 203 includes a non-transitory computer readable storage medium having computer readable code thereon, the medium including instructions in which a computer processor performs operations for rendering and displaying a 3D image of the specimen. The instructions also include determining an index of refraction associated with the regulated and illuminated first solution.

It should be understood that the foregoing description is only illustrative of the invention. Thus, various alternatives and modifications can be devised by those skilled in the art without departing from the invention. For example, the reflective surfaces 13A-13D can be flat planar mirrors or could be shaped with a slight curve on the bottom to capture the bottom view of object 101 at a lower level. Accordingly, the present invention is intended to embrace all such alternatives, modifications and variances that fall within the scope of the appended claims.

What is claimed is:

1. A multi-plane imaging apparatus for imaging multiple reflection planes of a regular or irregular shaped three-dimensional (3D) specimen, having top, side and bottom views simultaneously, the apparatus comprising:

A body, wherein the body comprises:
   a base having a base horizontal plane;
   an inverted watertight pyramid well having at least four reflective side surfaces for reflecting the specimen side views, wherein each of the at least four reflective sides surfaces define an angle, $\delta$, relative to the base horizontal plane, and wherein each reflective side surface comprises a plurality of reflective zones;

a specimen mounting apparatus positioned horizontally equidistant from the at least four reflective side surfaces and positioned vertically from the base horizontal plane a predetermined vertical distance;

wherein the predetermined vertical distance, the at least four reflective side surfaces, and the angle θ comprise a bottom reflection image plane for reflecting the specimen bottom views;

a solution controller for regulating a first solution in the inverted watertight pyramid well, wherein the solution controller further comprises a lighting apparatus for illuminating the specimen in the regulated first solution, wherein the lighting apparatus comprises an Ultra Violet (UV) lighting apparatus for exciting molecules within the specimen in the regulated first solution;

an imaging device, wherein the imaging device is disposed to capture the specimen top view, and the reflected side and bottom views substantially simultaneously; and a non-transitory computer readable storage medium having computer readable code thereon, the medium including instructions for determining an index of refraction associated with the regulated and illuminated first solution and instructions for rendering a 3D image of the specimen top view and the reflected side and bottom views as a function of the determined index of refraction associated with the regulated and illuminated first solution.

2. The multi-plane imaging apparatus as in claim 1 wherein the solution controller further comprises a temperature element for heating or cooling the regulated first solution.

3. The multi-plane imaging apparatus as in claim 1 wherein the imaging device comprises a fluorescence wavelength detector.

4. The multi-plane imaging apparatus as in claim 1 wherein the imaging device comprises a phosphorescence wavelength detector.

5. The multi-plane imaging apparatus as in claim 1 wherein the non-transitory computer readable storage medium having computer readable code thereon, further includes instructions comprising determining the angle of reflection for the plurality of reflective zones.

6. The multi-plane imaging apparatus as in claim 5 wherein the non-transitory computer readable storage medium having computer readable code thereon, further includes instructions comprising combining the captured the specimen top view, the reflected side and bottom views, the index of refraction associated with the regulated solution, and the angle of reflection for the plurality of reflective zones to render a 3D image.

7. The multi-plane imaging apparatus as in claim 1 further comprising the solution controller for regulating a second solution in the inverted watertight pyramid well.

8. A multi-plane imaging apparatus for imaging multiple reflection planes of a regular or irregular shaped three-dimensional (3D) specimen, having top, side and bottom views simultaneously, the apparatus comprising:

a body, wherein the body comprises:
 a base having a base horizontal plane;
 an inverted watertight pyramid well having at least four reflective side surfaces for reflecting the specimen side views, wherein each of the at least four reflective sides surfaces define an angle, θ, relative to the base horizontal plane, and wherein each reflective side surface comprises a plurality of reflective zones;

a specimen mounting apparatus positioned horizontally equidistant from the at least four reflective side surfaces and positioned vertically from the base horizontal plane a predetermined vertical distance;

wherein the predetermined vertical distance, the at least four reflective side surfaces, and the angle θ comprise a bottom reflection image plane for reflecting the specimen bottom views;

a solution controller for regulating a first solution in the inverted watertight, wherein the solution controller further comprises a temperature element for heating or cooling the regulated first solution;

a lighting apparatus for illuminating the specimen in the regulated first solution, wherein the lighting apparatus comprises an Ultra Violet (UV) lighting apparatus for exciting molecules within the specimen in the regulated first solution;

an imaging device, wherein the imaging device is disposed to capture the specimen top view, and the reflected side and bottom views substantially simultaneously; and a non-transitory computer readable storage medium having computer readable code thereon, the medium comprising:
 instructions for determining an index of refraction associated with the regulated and illuminated first solution and instructions for rendering a 3D image of the specimen top view and the reflected side and bottom views as a function of the determined index of refraction associated with the regulated and illuminated first solution;
 instructions comprising determining the angle of reflection for the plurality of reflective zones; and
 instructions comprising combining the captured the specimen top view, the reflected side and bottom views, the index of refraction associated with the regulated solution, and the angle of reflection for the plurality of reflective zones to render a 3D image.

9. The multi-plane imaging apparatus as in claim 8 wherein the imaging device comprises a fluorescence wavelength detector.

10. The multi-plane imaging apparatus as in claim 8 wherein the imaging device comprises a phosphorescence wavelength detector.

11. An image collection system for imaging multiple reflection planes of a regular or irregular shaped three-dimensional (3D) specimen having top, side and bottom views simultaneously, the apparatus comprising:

a well body, wherein the well body comprises:
 a plurality of reflection surfaces forming an inverted pyramid surrounding the specimen;
 a first solution input, port for immersing the specimen in a first fluid;
 a second solution input port for immersing the specimen in a second fluid;

a thermal controller for controlling the temperature of the first and second fluid;

an illumination system for illuminating the specimen in the first and second fluid; and a non-transitory computer readable storage medium having computer readable code thereon, the medium comprising:
 instructions for determining an index of refraction associated with the regulated and illuminated first solution and instructions for rendering a 3D image of the specimen top view and the reflected side and bottom views as a function of the determined index of refraction associated with the regulated and illuminated first solution;

instructions comprising determining the angle of reflection for the plurality of reflective zones; and instructions comprising combining the captured the specimen top view, the reflected side and bottom views, the index of refraction associated with the regulated solution, and the angle of reflection for the plurality of reflective zones to render a 3D image.

12. The image collection system as in claim 11 further comprising, a well cover adaptable to enclose the well body.

13. The image collection system as in claim 12 wherein the well cover comprises a light filter.

* * * * *